United States Patent [19]

Knifton et al.

[11] Patent Number: 4,822,921
[45] Date of Patent: Apr. 18, 1989

[54] METHOD FOR ONE-STEP SYNTHESIS OF METHYL T-BUTYL ETHER

[75] Inventors: John F. Knifton; Neal J. Grice, both of Austin, Tex.

[73] Assignee: Texaco Chemical Company, White Plains, N.Y.

[21] Appl. No.: 168,064

[22] Filed: Mar. 14, 1988

[51] Int. Cl.⁴ .............................................. C07C 41/09
[52] U.S. Cl. .................................................... 565/698
[58] Field of Search ........................................ 568/698

[56] References Cited

U.S. PATENT DOCUMENTS

| | | | |
|---|---|---|---|
| 2,282,469 | 5/1942 | Frolich | 568/698 |
| 3,816,550 | 6/1974 | Young et al. | 568/644 |

Primary Examiner—Howard T. Mars
Attorney, Agent, or Firm—Jack H. Park; Kenneth R. Priem; Cynthia L. Kendrick

[57] ABSTRACT

A method is disclosed for producing methyl tertiary butyl ether by reacting tertiary butyl alcohol and methanol in the presence of a catalyst comprising an inert support, such as titania, having a phosphoric acid impregnated thereon at a mild temperature and moderate pressure.

4 Claims, No Drawings

METHOD FOR ONE-STEP SYNTHESIS OF METHYL T-BUTYL ETHER

CROSS-REFERENCE

This application is related to U.S. patent application Ser. Nos. 07/168/063, 07/168,022 and 07/167/948, filed of even date.

This invention concerns an improved process for preparing methyl tertiary butyl ether by the reaction of tertiary butanol and methanol in the presence of a catalyst composition prepared by depositing a minor amount of phosphorus on titania. The invention is particularly advntageous in that the reaction takes place in one-step under relatively mild conditions, the catalyst exhibits excellent selectivity to the desired ether product, and high levels of tert-butanol conversion are achieved. The method could have commercial potential, the products do not require extensive distillation and the process uses an inexpensive, readily available feedstock. Typically, MTBE is generated continuously in ca. 30% concentration in the crude liquid product under relatively mild conditions by passage of 2:1 methanol/t-butanol over an extrudated phosphoric acid-on-titania catalyst.

BACKGROUND OF THE INVENTION

It is known to those skilled in the art that ethers, including unsymmetrical ethers, may be prepared by reacting an alcohol with another alcohol to form the desired product. The reaction mixture, containing a catalyst and/or condensing agent may be separated and further treated to permit attainment of the desired product. Such further treatment commonly includes one or more distillation operations.

Methyl tert-butyl ether is finding increasing use as a blending component in high octane gasoline as the current gasoline additives based on lead and manganese are phased out. Currently all commercial processes for the manufacture of methyl tert-butyl ether (MTBE) are based upon the liquid-phase reaction of isobutylene and methanol (eq. 1), catalyzed by a cationic ion-exchange resin (see, for example: hydrocarbon processing, Oct. 1984, p. 63; Oil and Gas J., Jan. 1, 1979, p. 76; Chem. Economics Handbook-SRI, September 1986, p. 543–705: P). The cationic ion-exchange resins used in MTBE synthesis normally have the sulphonic acid functionality (see: J. Tejero, J. Mol. Catal., 42 (1987) 257; C. Subramamam et al., (Can. J. Chem. Eng., 65 (1987) 613).

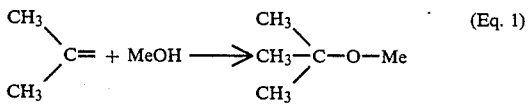

(Eq. 1)

With the expanding use of MTBE as an acceptable gasoline additive, however, a growing problem is the availability of raw materials. Historically, the critical raw material is isobutylene (Oil and Gas J., June 8, 1987, p. 55). It would be advantageous, therefore, to have a process to make MTBE that does not require isobutylene as a building block. Specifically, it would be advantageous to have an efficient process for making MTBE by reaction of methanol with tertiary butyl alcohol, since t-butanol (TBA) is readily available commercially through isobutane oxidation.

In U.S. Pat. No. 4,144,138 (1979) to Rao et al., there is disclosed a method for recovering methyl tertiary butyl ether from etherification reaction effluent by azeotropic distillation to recover methanol-ether azeotrope overhead which is water-washed to give pure ether raffinate, the latter being azeotropically distilled to yield ether-methanol overhead which is recycled to water washing.

The preparation of methyl tert-butyl ether from methyl and tert-butyl alcohols is discussed in S. V. Rozhkov et al., Prevrashch Uglevodorodov, Kislotno-Osnovn. Geterogennykh Katal. Tezisy Kokl. Vses Konf., 1977, 150 (C. A. 92:58165y). Here the TBA and methanol undergo etherification over KU-2 strongly acidic sulfopolystyrene cation-exchangers under mild conditions. This reference contains data on basic parameters of such a process. It is also pointed out that, although a plant for etherification over cation exchangers does not present any major problems, considerations include the fact that recycling large amounts of tert-butyl alcohol and methanol, as well as isobutylene, causes the scheme to be somewhat more expensive. Also, the progress of the reaction over cation exchanges is usually complicated by various adsorption and diffusion factors, by swelling phenomena, and by the variable distribution of the components between the solution and ion-exchanger phase. Furthermore, said acidic cation-exchangers with an organic (polystyrene or polymethacrylate) backbone generally have a very limited stability range with regard to operating temperatures, with temperatures above 120° C. normally leading to irreversible destruction of the resin and loss of catalytic activity.

It would be a substantial advance in the art if methyl tertiary butyl ether could be generated continuously from tertiary butyl alcohol and methanol in one step, rather than from methanol and isobutylene, using an inorganic, heterogeneous catalyst that is thermally stable to temperatures above 120° C., preferably to temperatures up to 200° C. It would also be advantageous if the catalyst alleviated some other problems which have discouraged commercialization, such as extra steps inherent in distillation.

SUMMARY OF THE INVENTION

In accordance with certain of its aspects, the novel method of this invention for preparing methyl tert-butyl ether from tertiary butyl alcohol and methanol in one-step comprises reacting tertiary butyl alcohol and methanol in the presence of a catalyst comprising a titania support having phosphoric acids impregnated thereon. In addition to the improvements outlined, an added feature is that the catalyst appears to be less sensitive to impurities in the feed than other catalysts.

DESCRIPTION OF THE INVENTION

Preparation of the MTBE product of this invention may be carried out typically by reacting tertiary butyl alcohol and methanol in the presence of an etherification catalyst deposited an inert support. The etherification is carried out in one step and the catalyst preferably comprises phosphoric acids on-titania supports.

The reaction can be represented by the following:

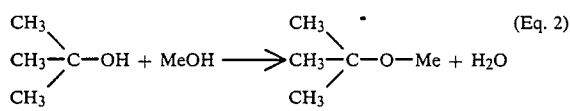

(Eq. 2)

Generally the methanol and t-butanol coreactants may be mixed in any proportion in order to generate the desired methyl t-butyl ether, but preferably the molar ratio of methanol to t-butanol in the feed mixture should be between 10:1 and 1:10, if the yield of desired MTBE is to be maximized. In order to achieve maximum selectivity to MTBE, and optimum conversion per pass, an excess of methanol in the liquid feed is desirable. The most preferred methanol-to-tertiary butanol molar ratio is from 1:1 to 5:1.

The same process may also be applied to the preparation of other alkyl tertiary alkyl ethers. For example, said process may be applied to the reaction of a $C_1$–$C_6$ primary alcohol such as methanol, ethanol, n-propanol and n-hexanol with a $C_4$–$C_{10}$ tertiary alcohol such as, for example, tertiary butanol and tertiary amyl alcohol. Reaction of methanol with tertiary amyl alcohol (2-methyl-2-butanol) would then yield methyl tertiary amyl ether (TAME). Alternatively a mixture of alcohols, e.g., a mixture of $C_1$–$C_5$ alcohols, could be reacted to give a mixture of alkyl tert-alkyl ethers.

The phosphorus impregnated on the catalyst in the instant invention should be present as a phosphoric acid or fluorophosphoric acid group which is chemically bound to the titania support. In the latter case, the exact nature of the bonding is not fully understood, but is believed to include, for the fluorophosphoric acid-on-titania catalyst, the following:

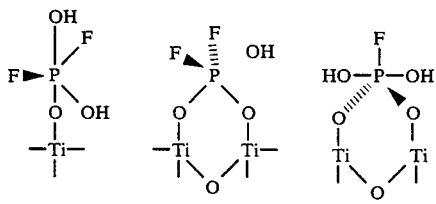

Said phosphorus may be introduced onto the inert support as phosphoric acid, $H_3PO_4$, as polyphosphoric acid and phosphorus acid, as well as phosphoryl halides such as phosphoryl chloride, $POCl_3$, or phosphoryl fluoride. The same phosphorus may also be introduced as a substituted phosphoric acid, such as a fluorophosphoric acid, including fluorophosphoric acid, $FPO_3H_2$ and difluorophosphoric acid $F_2PO_2H$. Also effective are alkylphosphonic acids such as methylphosphonic acid and ethylphosphonic acids, alkylphosphonic halides, such as ethylphosphonic dichloride and methylphosphonic fluoride, together with certain phosphates and phosphites including trimethylphosphite, diphenylphosphite, triethylphosphite, tributylphosphate, diphenylphosphate, and diethylbenzoylphosphate, and certain phosphonates such as triethylphosphonate, diethyl-n-heptylphosphonate, hexafluorophosphate, and di-n-octylphenylphosphonate. Ammonium hydrogen phosphates, including diammonium hydrogen phosphate, are also effective as phosphorus sources in the practice of this invention.

Mixtures of the phosphorus-containing compounds illustrated above may also be employed in the formulated catalyst.

Said phosphorus compounds may be introduced into the inert support in a liquid or gaseous form, in the presence, or absence, of an inert diluent.

The support should preferably comprise an inert compound. Compounds which could be employed are those containing elements of Group III and IV of the periodic table. Suitable compounds include the oxides of Al, Si, Ti and Zr, e.g. alumina, silica (silicon dioxide), titania (titanium dioxide) and zirconia, as well as combination thereof. Titania is preferred for the support and is demonstrated in the examples.

The inert support may be in the form of powders, pellets, spheres, shapes and extrudates. The examples described herein demonstrate the advantages of using pellets and extrudates. Titania pellets can be prepared by extrusion or by compaction in conventional pelleting apparatus using a pelleting aid such as graphite. An extrudate which works well is HSA titania carrier extrudate from Norton Company, with a surface area of 51 $m^2/g$.

As will be demonstrated by the examples, the supports are preferably of high purity and high surface area. It has been found in the process of this invention that greater conversion of tertiary butanol and methanol is achieved where the surface area of the support is generaly $>10$ $m^2/g$.

The pelleted catalyst compositions of the present invention are preferably employed as a fixed bed of catalyst in a continuous reaction system. In a continuous process of this nature, the time of contact of the reactants with the catalyst is one of the interrelated factors that those skilled in the art will adjust, along with temperature, pressure, bed geometry, pellet size, etc. in order to obtain a desired rate of reaction and, hence, a desired percentage of conversion of the reactants. Thus, in a continuous process, it is not necessary to drive the reaction to completion because unreacted feedstock components can be recycled to the reactor.

Cylindrically-shaped catalyst pellets having a diameter essentially equal to thelength thereof can be employed. Diameters and lengths ranging from about 0.794 mm (1/32 inch) to about 9.525 mm (⅜ inch) possess desirable dimensions. It will be understood that the shape and dimensions of the pellets are not critical to the present invention and that pellets of any suitable shape and dimensions may be used as desired by one wishing to practice the process of the present invention.

When cylindrical pellets of catalyst of the type described above are used, the weighted hourly space velocity may be varied within wide limits (e.g., 0.1 to 10 w/hr/w) in order to obtain a desired rate of conversion, as explained above. Normally, space velocities of about 0.5 to 2 w/hr/w will be employed.

Catalyst life is an important factor in conducting a continuous reaction. For example, if a catalyst is easily poisoned, or if catalyst pellets do not have good structural properties, the economics of the process will be adversely affected. The catalysts of the present invention are relatively insensitive to poisoning, so this should not present a problem.

As a consequence, the catalyst compositions of the present invention are advantageously used in a continuous process for the continuous production of methyl t-butyl ether reaction products from tertiary butanol and methanol. Such catalyst compositions can be used for prolonged periods without the need for regeneration. Nevertheless, with the passage of time deactivation will tend to slowly occur. Deactivation can be measured qualitatively by the loss of butanol conversion, or as the increase of temperature required to maintain an essentially constant conversion rate for the t-butanol and methanol.

Generally, the catalyst composition is prepared by impregnating a preformed pellet. A suitable procedure to be used is to immerse titania pellets in an aqueous or polar organic solvent (such as acetone) solution of the acid, preferably at ambient temperature. Higher temperatures of about 100° to about 150° C. can be used, if desired. This treatment should be continued, preferably with agitation, for about 0.1 to about 5 hours sufficient to permit the solution to penetrate the pores of the titania pellet. Suitably, the amount of solution of the acid that is used should be adequate to permit full immersion of the titania pellets. Larger amounts of the solution can be used, if desired, but there is no particular advantage in doing so. At the end of the immersion step, the excess solution can be evaporated from the treated pellets or the pellets can be removed from the solution and permitted to dry (e.g., in a drying oven).

The pelleted catalyst compositions of the present invention should be calcined. They can be calcined prior to use or possibly, in some cases, in situ, when used as catalysts at temperatures in excess of about 50° C. When the catalysts are to be calcined prior to use, calcination is suitable conducted for 2 to 24 hours at a temperature of at least 100° C., but below the temperature at which thermal destruction of the chemical bonding occurs. This can be determined by routine experimentation for a particular catalyst. Temperatures above 900° C. should be avoided. A suitable calcining temperature range is normally 100° to 800° C. and, more preferably, 150° to 350° C.

The weight percent of phosphoric acid to titania support should be such that the concentration of the phosphorus in the formulated catalyst is in the range of 0.1 wt% to 30 wt%, although concentrations outside this range may also be employed. Where phosphoric acid, for example, is supported on titania, a suitable quantity of phosphorus is 1–10 wt%. Where the phosphorus is in the form of fluorophosphoric acid or difluorophosphoric acid, a suitable quantity would be 1–10 weight percent.

The fact that this method can be achieved under relatively mild operating conditions is an attractive feature of this invention. Etherification can generally be conducted at temperatures from 20° C. to 200° C. The preferred range is 100° to 180° C. The total operating pressure may be from 0 to 1000 psig, or higher. The preferred pressure range is 50 to 500 psig.

Typically, MTBE is generated continuously in up to ca. 30 wt% concentration in the crude liquid product at total liquid hourly space velocities (LHSV) of at least 0.1 and up to ten, and relatively mild conditions, where:

$$LHSV = \frac{\text{Volume Of Total Liquid Feed Run Through The Reactor Per Hour}}{\text{Volume of Catalyst In Reactor}}$$

In particular, preparation of the catalyst of this invention involves impregnating the phosphoric acid onto the inert support using the incipient wetness technique in the following manner:

A solution of fluorophosphoric acid (8.6 g) in acetone (17.9 g) was added, with stirring, to 52.4 g of HSA titania carrier extrudate (from Norton Company, surface area 51 m$^2$/g). The liquid was absorbed onto the extrudates with periodic stirring and warming to 55° C. The mixture was then rotary evaporated to remove excess liquid and calcined at 150° C. for 40 minutes and 350° C. for 3 hours and 15 minutes under nitrogen flow.

Analyses showed the presence of:
3.0% phosphorus
0.6% fluorine

This sample was used in Example I and in the runs summarized in

TABLE I

The examples which follow illustrate the one-step synthesis of MTBE from TBA and MeOH (Eq. 2) using phosphorus-on-titania, particularly phosphoric acids and fluorophosphoric acids on high surface area titania. The examples are only intended as a means of illustration and it is understood the invention is not meant to be limited thereby.

Conversion of t-butanol (TBA, wt%) is estimated in the following examples using the equation:

$$\frac{(\text{Wt \% Conc. of } TBA \text{ in Feed} - \text{Wt \% Conc. of } TBA \text{ in Product})}{\text{Wt \% Conc. of } TBA \text{ in Feed}} \times 100$$

yields of methyl t-butyl ether (MTBE, mole %) are estimated from:

$$\frac{\text{Moles of } MTBE \text{ in Product Liquid}}{\text{moles of } TBA \text{ converted}} \times 100$$

EXAMPLE I

This example illustrates the cosynthesis of methyl t-butyl ether from t-butanol and methanol using a fluorophosphoric acid-on-titania catalyst.

The synthesis was conducted in a tubular reactor (0.563" id; 12" long), constructed of ;b 316 stainless steel, operated upflow and mounted in a furnace, controllable of ±1.0° C. and fitted with pumps allowing flow control to <1 cc/hr. The reactor was also fitted with a pressure regulating device and equipment for monitoring temperature, pressure and flow rate.

The reactor was charged at the beginning of the experiment with 25 cc of fluorophosphoric acid-on-titania catalyst the preparation of which was described above and identified as being used in Example I and the runs summarized in Table I. A screen of glass beads was placed at the top and bottom of the reactor to ensure the extrudates would remain in the middle portion. The catalyst bed was first conditioned overnight by treatment with methanol/t-butanol (2:1 mix) at 100° C., 300 psi back pressure and a liquid flow rate of 25 cc/hr. The same solution of methanol (1281.6 g, 40.0 mole) plus t-butanol (1482.4 g, 20.0 mole) was then pumped through the catalyst bed at 25 cc/hr, while the reactor was held at 100° C., at a total pressure of 300 psi. Samples of product were taken periodically, either by trapping in a dry ice cooled container, or by collecting on-stream (on-line) in a 316 ss bomb. Typical analyses data for samples taken under these conditions are summarized in Table I. Catalyst performance at other operating temperatures and liquid flow rates were also measured, after reaching equilibrium conditions overnight. Summary data for these runs are also given in Table I.

Of note is the fact that the fluorophosphoric acid-on-titania gave MTBE in concentrations up to ca. 26% concentration in the crude liquid product when run at LHSV of 1 (e.g. samples #13 and 15). The operating conditions in both cases (150° C., 300 psi) are moderate. This catalyst was screened over the temperature range 100°–180° C. At 150° C., LHSV=1, sample #15 shows:

Estimated TBA conversion per pass=66%

MTBE yield (basis TBA converted)=64 mole %

TABLE I

| Catalyst | | Feed Sample | Flow Rate (cc/hr) | Pressure (psig) | Temp. (°C.) | Sample | PRODUCT COMPOSITION (WT %)[c] | | | | |
|---|---|---|---|---|---|---|---|---|---|---|---|
| | | | | | | | MTBE | 1-C$_4$ | MeOH | tBA | H$_2$O |
| | | F | | | | | | | 47.0 | 52.4 | |
| Example I | (HO)$_2$P(O)F/[a] TiO$_2$ | | 25 | 300 | 100 | #1 | 3.2 | 1.9 | 45.9 | 48.2 | 0.7 |
| | | | | | | #5 | 2.7 | 0.5 | 46.6 | 49.4 | 0.7 |
| | | | | | | #6[b] | 2.9 | 0.6 | 45.5 | 51.0 | — |
| | | | " | " | 120 | #9 | 13.2 | 3.6 | 42.2 | 36.3 | 4.6 |
| | | | | | | #11 | 12.9 | 2.9 | 42.1 | 36.1 | 5.8 |
| | | | | | | #12[b] | 8.6 | 2.5 | 44.0 | 42.4 | 2.5 |
| | | | " | " | 150 | #13 | 26.1 | 8.5 | 38.4 | 14.8 | 12.1 |
| | | | | | | #15 | 26.2 | 5.3 | 38.7 | 17.7 | 11.9 |
| | | | | | | #19[b] | 25.0 | 8.7 | 37.2 | 19.9 | 9.2 |
| | | | " | " | 180 | #20 | 24.3 | 6.4 | 42.8 | 11.4 | 15.0 |
| | | | | | | #24 | 25.5 | 6.3 | 45.4 | 7.9 | 14.7 |
| | | | | | | #25[b] | 18.1 | 21.2 | 40.9 | 4.0 | 15.7 |

[a]Fluorophosphoric acid-on-titania, preparation as described above
[b]On-Line Sample
[c]i-C$_4$, Isobutylene; MeOH, Methanol; tBA, t-Butanol

EXAMPLE II

In this Example, following the procedures of Example I, methyl tert-butyl ether (MTBE) is generated from methanol and t-butanol (TBA) using a phosphoric acid-on-titanis catalyst prepared by a method similar to that described above. The same titania from the Norton Company was used as the inert support, and after treatment with phosphoric acid and calcination, the final phosphorus content of the formulated catalyst was 2.0%.

Data for the generation of MTBE from MeOH plus TBA using 25 cc of the phosphoric acid-on-titania catalyst and the equipment plus procedures of Example I, are summarized in Table II.

It may be noted that in this run series MTBE is generated in up to ca. 24% concentration in the crude liquid product when run at LHSV of 1 and moderate operating conditions (e.g. 180° C., 300 psi, see Sample #17).

TABLE II

| Catalyst | | Feed Sample | Flow Rate (cc/hr) | Pressure (psig) | Temp. (°C.) | Sample | PRODUCT COMPOSITION (WT %)[c] | | | | |
|---|---|---|---|---|---|---|---|---|---|---|---|
| | | | | | | | MTBE | i-C$_4$ | MeOH | tBA | H$_2$O |
| | | F | | | | | | | 46.3 | 52.8 | |
| Example II | H$_3$PO$_4$TiO$_2$[a] | | 25 | 300 | 100 | #1 | 0.6 | 0.3 | 47.2 | 51.2 | 0.6 |
| | | | | | | #5 | 0.4 | 0.1 | 47.6 | 51.7 | 0.1 |
| | | | | | | #6[b] | 0.6 | 0.2 | 47.5 | 51.6 | — |
| | | | " | " | 150 | #7 | 7.7 | 3.5 | 44.0 | 41.6 | 3.0 |
| | | | | | | #11 | 7.0 | 2.0 | 45.0 | 43.0 | 2.9 |
| | | | | | | #12[b] | 7.0 | 2.8 | 44.8 | 43.1 | 2.3 |
| | | | " | " | 180 | #14 | 22.6 | 17.3 | 37.3 | 9.1 | 13.5 |
| | | | | | | #17 | 24.2 | 13.0 | 39.5 | 9.2 | 14.1 |
| | | | | | | #18[b] | 22.1 | 15.6 | 39.0 | 10.9 | 12.5 |

[a]Phosphoric acid-on titania, prepared as described above
[b]On-Line Sample

EXAMPLE III

In this Example, following the procedures of Example I, MTBE is generated from methanol and t-butanol using a difluorophosphoric acid-on-titania catalyst prepared by a method similar to that described above. The same titania from Norton Company was used as the inert support, and after treatment with difluorophosphoric acid and calcination, analyses showed 0.6% phosphorus and 0.5% fluorine content.

Data for the generation of MTBE from MeOH plus TBA using 25 cc of the difluorophosphoric acid-on-titania catalyst and the equipment plus procedures of Example I, are summarized in Table III.

Here it may be seen that after screening this catalyst over the 100°–800° C. temperature range, that at a LHSV of 1, MTBE may be generated in up to ca. 29% concentration in the crude liquid product (see Example #20):

Estimated TBA conversion per pass=81%

MTBE yield (basis TBA converted)=55 mole%

TABLE III

| | Catalyst | Feed Sample | Flow Rate (cc/hr) | Pressure (psig) | Temp. (°C.) | Sample | PRODUCT COMPOSITION (WT %) | | | | |
|---|---|---|---|---|---|---|---|---|---|---|---|
| | | | | | | | MTBE | i-C$_4$ | MeOH | tBA | H$_2$O |
| Example III | HPO$_2$F$_2$/[a] TiO$_2$ | F | 25 | 300 | 100 | #1 | 1.5 | 0.6 | 46.4 | 46.0 | 51.5 | 53.5 | 0.3 |
| | | | | | | #3 | 1.1 | 0.1 | 46.1 | 52.2 | 0.4 |
| | | | | | | #6[b] | 1.7 | 0.2 | 45.9 | 52.2 | — |
| | | | " | " | 120 | #8 | 2.2 | 0.5 | 46.0 | 51.0 | 0.3 |
| | | | | | | #12 | 2.0 | 0.4 | 46.0 | 51.1 | 0.4 |
| | | | | | | #13[b] | 2.3 | 0.5 | 45.9 | 51.3 | — |
| | | | " | " | 150 | #15 | 14.4 | 3.0 | 41.8 | 37.0 | 3.8 |
| | | | | | | #18 | 13.8 | 3.6 | 41.6 | 37.3 | 3.6 |
| | | | | | | #19[b] | 13.3 | 3.8 | 41.8 | 38.0 | 3.0 |
| | | | " | " | 180 | #20 | 28.5 | 12.3 | 39.0 | 10.1 | 10.1 |
| | | | | | | #24 | 25.8 | 13.1 | 39.4 | 9.7 | 11.9 |
| | | | | | | #25[b] | 25.2 | 17.7 | 37.6 | 8.9 | 10.6 |

[a]Difluorosphoric acid-on-titania, prepared as described above
[b]On line sample

What is claimed is:

1. A method for synthesizing methyl t-butyl ether from t-butanol and methanol in one step wherein methyl t-butyl ether is synthesized from a 5:1 to 1:1 molar mix of methanol and t-butanol, over a fluorophosphoric acid-on-titania supported catalyst having a phosphorus content in the range of 1–10 wt%, at an operating temperature of 100°–180° C., an operating pressure of 50 to 500 psi, and a methanol plus t-Butanol LHSV in the range 0.1 to 10.

2. The method of claim 1 wherein the fluorophosphoric acid is selected from the group consisting of fluorophosphoric acid FPO$_3$H$_2$, and difluorophosphoric acid, F$_2$PO$_2$H.

3. The method of claim 1 wherein the titania support is in a shape from the group consisting of pellets and extrudates.

4. The method of claim 3 wherein the titanium support has a surface area of greater than 10 m$^2$/g.

* * * * *